United States Patent
Bonifazi et al.

(10) Patent No.: US 9,040,749 B2
(45) Date of Patent: May 26, 2015

(54) BORAZINE DERIVATIVES

(75) Inventors: Davide Bonifazi, Reggio Emilia (IT); Simon Kervyn De Meerendre, Autre-Eglise (BE); Franco Cacialli, London (IT); Oliver Fenwick, London (GB)

(73) Assignees: UNIVERSITE DE NAMUR, Namur (BE); UCL BUSINESS PLC, London (GB)

(*) Notice: Subject to any disclaimer, the term of this patent is extended or adjusted under 35 U.S.C. 154(b) by 0 days.

(21) Appl. No.: 14/006,078

(22) PCT Filed: Mar. 16, 2012

(86) PCT No.: PCT/EP2012/054670
§ 371 (c)(1),
(2), (4) Date: Oct. 16, 2013

(87) PCT Pub. No.: WO2012/126832
PCT Pub. Date: Sep. 27, 2012

(65) Prior Publication Data
US 2014/0088324 A1  Mar. 27, 2014

(30) Foreign Application Priority Data
Mar. 18, 2011 (EP) .................................... 11158909

(51) Int. Cl.
*C07F 5/05* (2006.01)
*H01L 51/00* (2006.01)
*H01L 51/50* (2006.01)

(52) U.S. Cl.
CPC ............. *H01L 51/005* (2013.01); *C07F 5/05* (2013.01); *H01L 51/008* (2013.01); *H01L 51/5012* (2013.01); *H01L 51/5032* (2013.01)

(58) Field of Classification Search
None
See application file for complete search history.

(56) References Cited

U.S. PATENT DOCUMENTS

2005/0153164 A1   7/2005  Che et al.

FOREIGN PATENT DOCUMENTS

| JP | 2005-170857 | 6/2005 |
|---|---|---|
| JP | 2010-280637 | 12/2010 |
| WO | WO 2005/068583 | 7/2005 |

OTHER PUBLICATIONS

Madura et al Tetrahedron (1998), 54(49), 14913-14918.*
Mikhailov et al. Zhurnal Obshchei Khimii 1959, 29, 1477-83.*
Brown et al., "Efficient electron injection in blue-emitting polymer light-emitting diodes with LiF/Ca/Al cathodes", *Applied Physics Letters*, vol. 79, No. 2, 2001, pp. 174-176.
Brown et al., "Contact Optimization in Polymer Light-Emitting Diodes", *Journal of Polymer Science: Part B: Polymer Physics*, vol. 41, 2003, pp. 2649-2664.
Meller et al., "Fluoralkyl- and Fluorarylborazinderivative, 1.Mitt", *Mh. Chem.*, vol. 97, No. 2, 1966, pp. 388-395.
Wakamiya et al., "Toward π-Conjugated Molecule Bundles: Synthesis of a Series of B,B', B"-Trianthryl-N,N', N"-triarylborazines and the Bundle Effects on Their Properties", *J. Am. Chem. Soc.*, vol. 127, 2005, pp. 14859-14866.
Bielawski et al., "Reactions of Borazines with Pyrazole and Related Studies: (μ-Amido)(μ-pyrazolato) diboron Species, Novel Relatives of the Pyrazaboles", *Inorg. Chem.*, vol. 25, 1986, pp. 4623-4628.
International Search Report and Written Opinion from International Application No. PCT/EP2012/054670 mailed May 7, 2012.
Gerrard, W., "The experimental approach to the preparation of applicable borazole polymers", *Sci Monograph*, vol. 13, 1961, pp. 328-342. XP002659843.
Johnson et al., "Atropisomerism in Aryl-Substituted Borazines", *Inorganic Chemistry*, vol. 13, No. 11, 1974, pp. 2769-2772.
Korshak et al., "Reaction of 1,2-diphenyldiborane with amines and organo-borodiamines", XP00265842, 1963, 1645-8.
Paetzold et al., "Boron Imides from the Thermal Decomposition of Diarylazidoboranes", *Chem. Ber.*, vol. 116, 1983, pp. 1531-1539.

* cited by examiner

*Primary Examiner* — Yong Chu
*Assistant Examiner* — Ana Z Muresan
(74) *Attorney, Agent, or Firm* — Merchant & Gould P.C.

(57) ABSTRACT

Borazine derivatives are used in the manufacture of electronic devices, in particular electroluminescent and semiconductor devices. More specifically, stable borazine derivatives include boron atoms substituted by aryl groups used in one or more layers of an electroluminescent or a semiconductor device, in particular in the emissive layer of organic light-emitting devices (OLED).

13 Claims, 7 Drawing Sheets

FIG.6 (a and b)

FIG. 7 (a and b)

BORAZINE DERIVATIVES

This application is a National Stage Application of PCT/EP2012/054670, filed 16 Mar. 2012, which claims benefit of Serial No. 11589099.9, filed 18 Mar. 2011 in Europe and which applications are incorporated herein by reference. To the extent appropriate, a claim of priority is made to each of the above disclosed applications.

TECHNICAL FIELD OF THE INVENTION

The present invention is directed to new borazine derivatives and their use in the manufacture of electronic devices, in particular electroluminescent and semiconductor devices. More specifically, the present invention relates to new stable borazine derivatives comprising boron atoms substituted by aryl groups and to their use in one or more layers of an electroluminescent or a semiconductor device, in particular in the emissive layer of organic light-emitting devices (OLED).

BACKGROUND OF THE INVENTION

With the general aim of reducing energy consumption through the planet, an important focus of research has been directed to organic and polymer electroluminescent materials which have emerged as valuable alternatives to the production of incandescent light. The ever-growing interest in the research and development of OLED has been mainly motivated by their extended use in flat panel display technology.

While many research groups have oriented their studies towards white light production, finding reliable and efficient UV light sources has appeared as being of high interest in various domains, such as optical storage, photocatalysis, sterilization and disinfection, and various surgical methods or medical treatments such as ophthalmic surgery or epilepsy treatment.

Production of UV light by organic materials is much more challenging than white light (Visible) production due to the very few organic molecules known to emit in the UV with a quantum yield acceptable for the production of light-emitting devices.

Whereas inorganic material-based LED emitting in the UV are known, the latter have several disadvantages compared to their organic counterparts. These disadvantages include, but are not limited to, non-tunability of the electronic density of the corresponding material, and broad UV emission due to the crystal lattice in which the inorganic emitter is formed.

In that context, borazine materials have recently emerged as a new class of promising materials with alleged high electron and hole mobility for applications in electroluminescent devices. In particular, WO 2005/068583 discloses borazine-containing material with allegedly high hole and electron mobility and thermal stability, which can allegedly be used in one or more layers of an electroluminescent device, including OLED or PLED devices. These devices are allegedly claimed to be capable of emitting light in the UV or visible regions.

JP2005-170857 discloses a series of B,B,B"-trianthryl-N,N,N"-triarylborazine derivatives and which are capable of emitting in the UV-Visible region with fairly high quantum yields. Although their potential utility as a core framework for organic electronic device applications has been evoked, it remains that the fluorescence properties of the corresponding derivatives is mainly due to the anthracenyl moieties which may considerably reduce the potential electronic fine-tuning properties of the disclosed borazine derivatives and interfere with the fluorescence originating from the borazine ring.

Meller et al. in "Fluoralkyl- und Fluorarylborazinderivate, 1.Mitt.", published in Monatshefte fuer Chemie (1966), 97(2), 619-32, pages 388-395, discloses merely the synthesis and IR spectra of various N-Fluoroalkyl- and B-Fluoroarylborazines, including B,B,B"-pentafluorophenyl-N,N,N"-triphenylborazine derivatives.

Without contesting advantages associated with the use of borazine derivative materials described in the art, there is still a need for new stable borazine derivatives with improved properties.

AIMS OF THE INVENTION

It is an aim of the present invention to provide new air-stable borazine derivatives which are capable of emitting in the UV region.

Advantageously, the borazine derivatives according to the invention are capable of emitting in the UV region with high quantum yield.

Advantageously still, the borazine derivatives according to the invention have substituents which allow fine-tuning the electronic properties of the borazine derivatives. Yet advantageously, the electronic properties of the borazine derivatives according to the invention are fine-tunable without interfering or perturbing whatsoever with the fluorescence/emission originating from the borazine ring.

It is still another advantage that the borazine derivatives of the invention possess high charge carrier mobility and are easy to synthesize, while providing excellent processability (such as e.g. solution processing, continuous printing) and excellent stability under atmospheric/ambient conditions.

Advantageously still, the borazine derivatives of the invention have excellent stability against hydrolysis.

Advantageously, the borazine derivatives according to the invention are suitable for use in the emissive layer of an electroluminescent device, in particular an organic light-emitting devices (OLED).

Other aims of the invention will be immediately apparent to those skilled in the art from the following description.

SUMMARY OF THE INVENTION

The present invention concerns borazine derivatives having the formula (II):

wherein the substituents $R^1$ to $R^{18}$ are the same or different from each other;

wherein each of $R^1$ to $R^{18}$ is independently selected from the group consisting of: hydrogen; linear or branched saturated alkyl group; linear or branched unsaturated alkyl group; cycloalkyl group; aryl group; aralkyl group; heteroaryl group; acyl group; hydroxyl; alkoxy group; aryloxy group; acyloxy group; amino group; alkylamino group; arylamino group; acylamino group; cyano group; carboxyl group; thio group; aminocarbonyl group; carbamoyl group, arlyoxycarbonyl group, phenoxycarbonyl group, alkoxycarbonyl group and halogen;

wherein $R^4$, $R^8$, $R^9$, $R^{13}$, $R^{14}$ and $R^{18}$ cannot simultaneously be selected to be hydrogen;

wherein $R^4$ to $R^8$ and $R^{14}$ to $R^{18}$ cannot simultaneously be selected to be fluorine; and wherein $R^1$, $R^2$ and $R^3$ cannot simultaneously be selected to be methyl;

wherein the substituents $R^{19}$ to $R^{27}$ are the same or different from each other;

wherein each of $R^{19}$ to $R^{27}$ is independently selected from the group consisting of: hydrogen; linear or branched saturated alkyl group; linear or branched unsaturated alkyl group; cycloalkyl group; aryl group; aralkyl group; heteroaryl group; acyl group; hydroxyl; alkoxy group; aryloxy group; acyloxy group; amino group; alkylamino group; arylamino group; acylamino group; cyano group; carboxyl group; thio group; aminocarbobyl group; carbamoyl group, arlyoxycarbonykl group, phenoxycarbonyl group, alkoxycarbonyl group and halogen; and wherein at least one substituent, preferably all the substituents selected from the group of $R^6$, $R^{11}$ and $R^{16}$ are independently selected from the group consisting of linear or branched saturated alkyl groups, preferably with 1 to 6 carbon atoms, more preferably with 1 to 4 carbon atoms, even more preferably with 1 to 3 carbon atoms.

Preferably, in said derivatives, at least one substituent, preferably all the substituents selected from the group of $R^{22}$, $R^{23}$, $R^{24}$, $R^{25}$, $R^{26}$ and $R^{27}$ are independently selected to be hydrogen.

Preferably, in the derivatives according to the invention, at least two substituents, preferably all the substituents selected from the group of $R^4$, $R^8$, $R^9$, $R^{13}$, $R^{14}$ and $R^{18}$ are independently selected from the group consisting of linear or branched saturated alkyl groups, preferably with 1 to 6 carbon atoms, more preferably with 1 to 4 carbon atoms, even more preferably with 1 to 3 carbon atoms.

Preferably, in the borazine derivatives of the invention, at least one substituent, preferably all the substituents selected from the group of $R^{19}$, $R^{20}$ and $R^{21}$ are independently selected from the group consisting of hydrogen, and linear or branched saturated alkyl groups, preferably with 1 to 12 carbon atoms, more preferably with 1 to 6 carbon atoms, even more preferably with 1 to 3 carbon atoms.

Preferably, in said derivatives, each of $R^1$ to $R^3$ and $R^{28}$ is independently selected from the group consisting of hydrogen, linear or branched saturated alkyl group, cycloalkyl group, aryl group and aralkyl group.

Preferably, the borazine derivatives according to the present invention are able to emit in the UV region with a quantum yield above 0.05, preferably above 0.3, more preferably above 0.4, even more preferably above 0.5, most preferably above 0.6.

In another aspect of the present invention, it is provided a method for the manufacture of an electronic device comprising the step of including a derivative as disclosed hereabove, the electronic device being preferably selected from the group consisting of electroluminescent and semiconductor devices.

Preferably, in said method, the electronic device is an OLED, and the derivative is preferably included in the emissive layer of said OLED.

Preferably, in the method according to the invention, the electronic device is a semiconductor device, preferably a transistor.

The present invention also concerns the use of a borazine derivative as disclosed hereabove for the manufacture of an electronic device, preferably for the manufacture of a device selected from the group consisting of electroluminescent and semiconductor devices.

Preferably, in said use, the electronic device is an OLED, and the derivative is preferably used for the manufacture of the emissive layer of said OLED.

Alternative, in said use, the electronic device is a semiconductor device, preferably a transistor.

The present invention thus also relates to an electronic device comprising a borazine derivative as disclosed hereabove.

Preferably, said electronic device is selected from the group consisting of electroluminescent devices and semiconductor devices.

Preferably, said electronic device is an OLED comprising at least one emissive layer, said emissive layer comprising the borazine derivative.

In the present description, the term "OLED" refers to organic light-emitting devices comprising an organic electroluminescent medium, with thickness of the order of about 100 nm, sandwiched between two electrodes. The most commonly used device configurations of OLED are of three different types: single layer type, double layer type and multilayer type. OLED of single layer type have only a single electroluminescent layer between the anode and the cathode. OLED of double layer type comprise two layers which are responsible for transporting holes and electrons, respectively. One of the hole-transporting layer or the electron-transporting layer is also the emitting layer. In a multilayer device, an emitting layer is inserted between the hole-transporting layer and the electron-transporting layer; said device may further comprise other layers, with other functionalities, such as hole-blocking layers, electron-blocking layers, and/or layers acting as "steps" to its adjacent layer.

In the present invention, providing electroluminescent devices with enhanced performances includes but is not limited to providing electroluminescent devices with high purity color, efficiency and low driving voltage.

Electroluminescent devices according to the invention, and in particular OLED, can be obtained by means of different techniques known by the man skilled in the art, in particular with vapor deposition, spin-coating, inkjet printing processes and the like.

BRIEF DESCRIPTION OF THE DRAWINGS

FIG. 6a gives the current-voltage-light characteristics of a light-emitting electrochemical cell comprising an active layer of N-triphenyl-B-trimesityl as the emitter, blended with poly (ethylene oxide) (PEO) as the ion transporter and lithium triflate (LiTr) as the salt providing mobile ions. The 3.5 mm² device was fabricated with a vertical structure ITO\PEDOT:PSS (80 nm)\active layer\liF (6 nm)\Ca (30 nm)\Al (150 nm), which is indicated schematically as an inset.

FIG. 6b represents the electroluminescence spectrum obtained at a bias of 17 V of the device tested in FIG. 6a.

The abbreviations PEDOT and PSS refer to poly(3,4-ethylene dioxythiophene) and to poly(styrene sulfonate), respectively. It means that PEDOT is doped with PSS and that a PEDOT:PSS film is incorporated between the ITO electrode and the emissive layer.

The anode of the structure comprises ITO or indium tin oxide, while the cathode comprise LiF/Ca/Al.

DETAILED DESCRIPTION OF THE INVENTION

According to one aspect of the present invention, it is provided a borazine derivative of the formula (I):

(I)

wherein the substituents $R^1$ to $R^{18}$ are the same or different from each other;
wherein each of $R^1$ to $R^{18}$ is independently selected from the group consisting of: hydrogen; linear or branched saturated alkyl group; linear or branched unsaturated alkyl group; cycloalkyl group; aryl group; aralkyl group; heteroaryl group; acyl group; hydroxyl; alkoxy group; aryloxy group; acyloxy group; amino group; alkylamino group; arylamino group; acylamino group; cyano group; carboxyl group; thio group; aminocarbonyl group; carbamoyl group, arlyoxycarbonyl group, phenoxycarbonyl group, alkoxycarbonyl group and halogen;

wherein n=1;
wherein $R^4$, $R^8$, $R^9$, $R^{13}$, $R^{14}$ and $R^{18}$ cannot simultaneously be selected to be hydrogen;
wherein $R^4$ to $R^8$ and $R^{14}$ to $R^{18}$ cannot simultaneously be selected to be fluorine; and
wherein $R^1$, $R^2$ and $R^3$ cannot simultaneously be selected to be methyl.

In other words, according to one aspect of the present invention, it is provided a borazine derivative having the formula (Ia):

Ia

Preferably, in the derivative of the invention, the borazine derivative has the formula (II):

(II)

wherein the substituents $R^4$ to $R^{18}$ are as defined hereinabove;
wherein the substituents $R^{19}$ to $R^{27}$ are the same or different from each other; and
wherein each of $R^{19}$ to $R^{27}$ is independently selected from the group consisting of: hydrogen; linear or branched saturated alkyl group; linear or branched unsaturated alkyl group; cycloalkyl group; aryl group; aralkyl group; heteroaryl group; acyl group; hydroxyl; alkoxy group; aryloxy group; acyloxy group; amino group; alkylamino group; arylamino group; acylamino group; cyano group; carboxyl group; thio group; aminocarbobyl group; carbamoyl group, arlyoxycarbonykl group, phenoxycarbonyl group, alkoxycarbonyl group and halogen.

Preferably, in the borazine derivative of the invention as described above, at least one substituent, preferably all the substituents, selected from the group of $R^{22}$, $R^{23}$, $R^{24}$, $R^{25}$, $R^{26}$ and $R^{27}$ are independently selected to be hydrogen.

Preferably, in the borazine derivatives of the invention, at least two substituents, preferably all the substituents, selected from the group of $R^4$, $R^8$, $R^9$, $R^{13}$, $R^{14}$ and $R^{18}$ are independently selected from the group consisting of linear or branched saturated alkyl groups, preferably with 1 to 6 carbon atoms, more preferably with 1 to 4 carbon atoms, even more preferably with 1 to 3 carbon atoms. Still more preferably, in the borazine derivatives of the invention, at least two substituents, preferably all the substituents selected from the group of $R^4$, $R^8$, $R^9$, $R^{13}$, $R^{14}$ and $R^{18}$ are independently selected from the group consisting of methyl, ethyl, and isopropyl groups.

Preferably, in the borazine derivatives of the invention, at least one substituent, preferably all the substituents, selected from the group of $R^6$, $R^{11}$ and $R^{16}$ are independently selected from the group consisting of linear or branched saturated alkyl groups and halogens; preferably from the group consisting of linear or branched saturated alkyl groups with 1 to 6 carbon atoms, more preferably with 1 to 4 carbon atoms, even more preferably with 1 to 3 carbon atoms.

Still more preferably, in the borazine derivatives of the invention, at least one substituent, preferably all the substituents, selected from the group of $R^6$, $R^{11}$ and $R^{16}$ are independently selected from the group consisting of methyl, ethyl and isopropyl groups.

Preferably, in the borazine derivatives of the invention, at least one substituent, preferably all the substituents, selected from the group of $R^{19}$, $R^{20}$ and $R^{21}$ are independently selected from the group consisting of hydrogen, and linear or branched saturated alkyl groups, preferably with 1 to 12 carbon atoms, more preferably with 1 to 6 carbon atoms, even more preferably with 1 to 3 carbon atoms. More preferably, in the borazine derivative of the invention, at least one substituent, preferably all the substituents, selected from the group of $R^{19}$, $R^{11}$ and $R^{21}$ are independently selected from the group consisting of hydrogen and dodecyl groups.

Preferably, in the borazine derivatives of the invention, each of $R^1$ to $R^3$ is independently selected from the group consisting of hydrogen, linear or branched saturated alkyl group, cycloalkyl group, aryl group and aralkyl group. More preferably, in the borazine derivatives of the invention, each of $R^1$ to $R^3$ is independently selected from the group consisting of hydrogen, isopropyl, cyclohexyl and phenyl groups.

Preferably, the (borazine) derivative of the invention is according to formula (II), wherein $R^4$, $R^6$, $R^8$, $R^9$, $R^{11}$, $R^{13}$, $R^{14}$, $R^{16}$ and $R^{18}$ are methyl groups; and wherein $R^5$, $R^7$, $R^{10}$, $R^{12}$, $R^{15}$, $R^{17}$ and $R^{19}$ to $R^{27}$ are selected to be hydrogen.

Preferably, the borazine derivative of the invention is according to formula (II), wherein $R^4$, $R^6$, $R^8$, $R^9$, $R^{11}$, $R^{13}$, $R^{14}$, $R^{16}$ and $R^{18}$ are methyl groups; wherein $R^5$, $R^7$, $R^{10}$, $R^{12}$, $R^{11}$ and $R^{17}$ and $R^{22}$ to $R^{27}$ are selected to be hydrogen; and wherein $R^{19}$, $R^{20}$, $R^{21}$ are dodecyl groups.

According to another aspect, the present invention relates to an electronic device comprising at least one layer comprising a borazine derivative as described above, wherein the electronic device is preferably selected from the group consisting of electroluminescent and semiconductor devices.

In a preferred aspect, the electronic device of the invention is an OLED, wherein said layer is preferably the emissive layer.

In another preferred aspect, the electronic device of the invention is a semiconductor device. More preferably, the electronic device of the invention is a transistor.

According to still another aspect of the present invention, it is provided a method for the manufacture of an electronic device which comprises the step of including a borazine derivative as described above, wherein the electronic device is preferably selected from the group consisting of electroluminescent and semiconductor devices.

Preferably, in the method of the present invention, the electronic device is an OLED. More preferably, in the method of the present invention the borazine derivative is included in the emissive layer of the OLED.

Preferably still, in the method of the present invention, the electronic device is a semiconductor device, more preferably a transistor.

According to still another aspect, the present invention relates to the use of a borazine derivative as described above for the manufacture of an electronic device. Preferably, the borazine derivative of the invention is used for the manufacture of a device selected from the group consisting of electroluminescent and semiconductor devices.

In a preferred aspect, the borazine derivative of the invention is used for the manufacture of an OLED, wherein the borazine derivative is preferably used for the manufacture of the emissive layer of the OLED.

In another preferred aspect, the borazine derivative of the invention is used for the manufacture of a semiconductor device, preferably a transistor.

According to one aspect of the present invention, it is provided a borazine derivative of the formula (I):

wherein the substituents $R^1$ to $R^{18}$ are the same or different from each other;

wherein each of $R^1$ to $R^{18}$ is independently selected from the group consisting of: hydrogen; linear or branched saturated alkyl group; linear or branched unsaturated alkyl group; cycloalkyl group; aryl group; aralkyl group; heteroaryl group; acyl group; hydroxyl; alkoxy group; aryloxy group; acyloxy group; amino group; alkylamino group; arylamino group; acylamino group; cyano group; carboxyl group; thio group; aminocarbonyl group; carbamoyl group, arlyoxycarbonyl group, phenoxycarbonyl group, alkoxycarbonyl group and halogen;

wherein n=1;

wherein $R^4$, $R^8$, $R^9$, $R^{13}$, $R^{14}$ and $R^{18}$ cannot simultaneously be selected to be hydrogen;

wherein $R^4$ to $R^8$ and $R^{14}$ to $R^{18}$ cannot simultaneously be selected to be fluorine; and wherein $R^1$, $R^2$ and $R^3$ cannot simultaneously be selected to be methyl.

In other words, the present invention is related to borazine derivatives having the general formula (Ia):

In the context of the present invention, it has been surprisingly found that the borazine derivatives according to the invention exhibit excellent stability to air, which includes resistance to oxidation, hydrolysis, degradation or decomposition under atmospheric/ambient conditions.

Without wishing to be bound by theory, it is believed that this excellent stability is due to the steric hindrance around the boron atoms created by the particular substituents depicted in formula (I) above. It is in particular believed that the presence of group substituents based on (substituted) phenyl moieties, as defined above, creates particularly efficient steric protection around the boron atoms of the borazine derivatives of the invention on which they are substituted.

Also, it is believed that the presence of at least one substituent in (preferably all) the ortho positions of the phenyl groups linked to the boron atoms of the borazine derivatives of the invention plays a substantial role in protecting the boron atoms against in particular nucleophilic attacks.

In some preferred aspects of the borazine derivatives of the invention, the particular substituents present on the nitrogen atoms may participate in creating further improved steric protection around the boron atoms of the borazine derivatives of the invention.

Preferably, in the derivative of the invention, n=1 and the borazine derivative has the formula (II):

wherein the substituents $R^4$ to $R^{18}$ are as defined hereinabove; wherein the substituents $R^{19}$ to $R^{27}$ are the same or different from each other; and wherein each of $R^{19}$ to $R^{27}$ is independently selected from the group consisting of: hydrogen; linear or branched saturated alkyl group; linear or branched unsaturated alkyl group; cycloalkyl group; aryl group; aralkyl group; heteroaryl group; acyl group; hydroxyl; alkoxy group; aryloxy group; acyloxy group; amino group; alkylamino group; arylamino group; acylamino group; cyano group; carboxyl group; thio group; aminocarbobyl group; carbamoyl group, arlyoxycarbonykl group, phenoxycarbonyl group, alkoxycarbonyl group and halogen.

Figure 1:
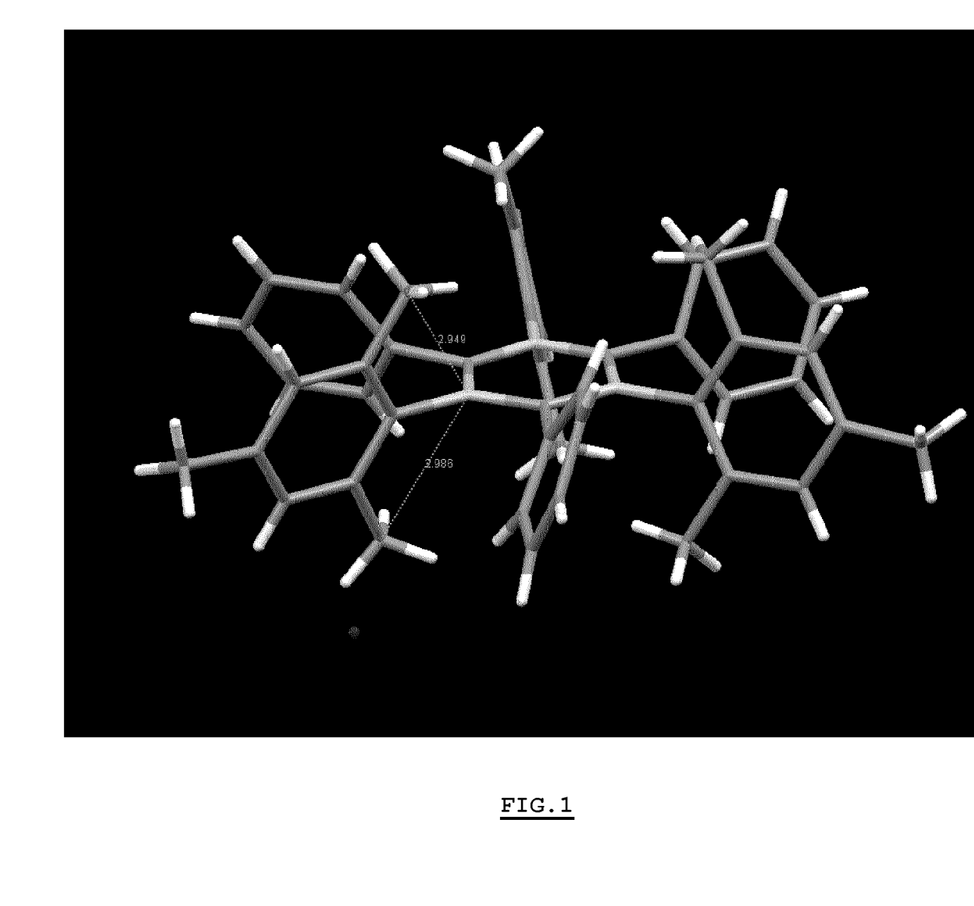
FIG. 1 represents the crystal structure of borazine derivative (1) showing the short carbon-boron distance, wherein the methyl groups are believed to protect the boron from a nucleophilic attack.
Figure 2:
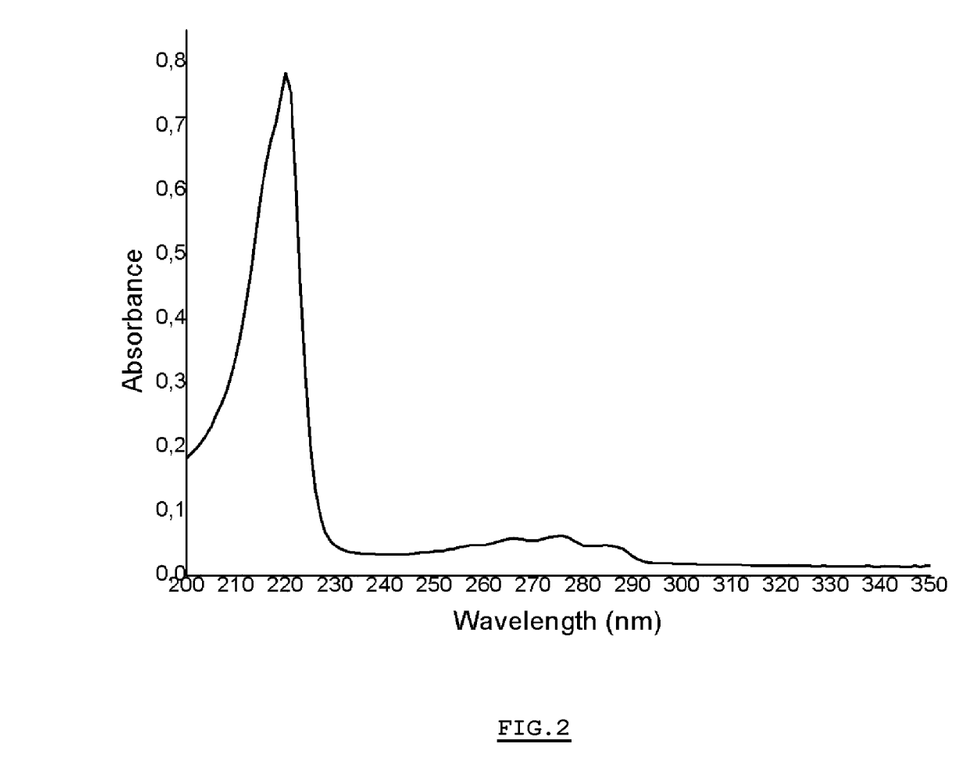
FIG. 2 represents UV absorption spectra of borazine derivative (1) showing the absorption maxima at 222 nm.
Figure 3:
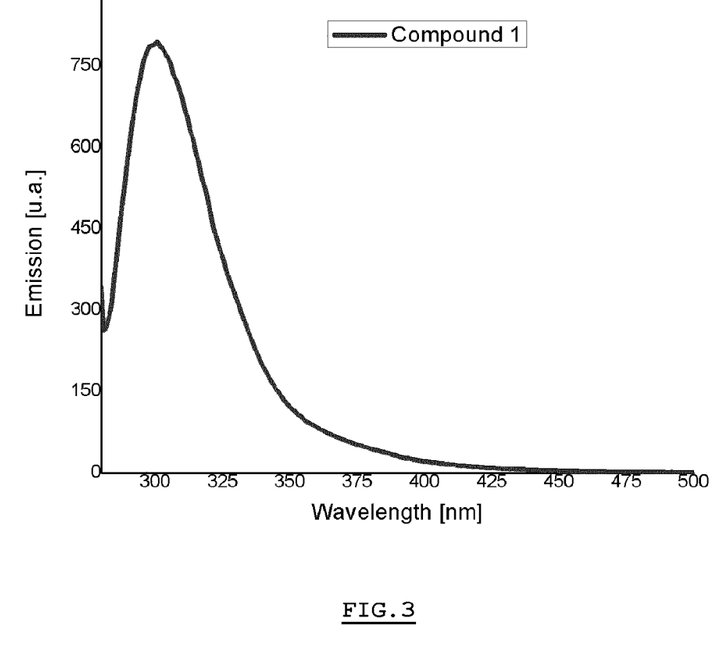
FIG. 3 represents the emission spectra of borazine derivative (1) in solution at 300 nm.
Figure 4:
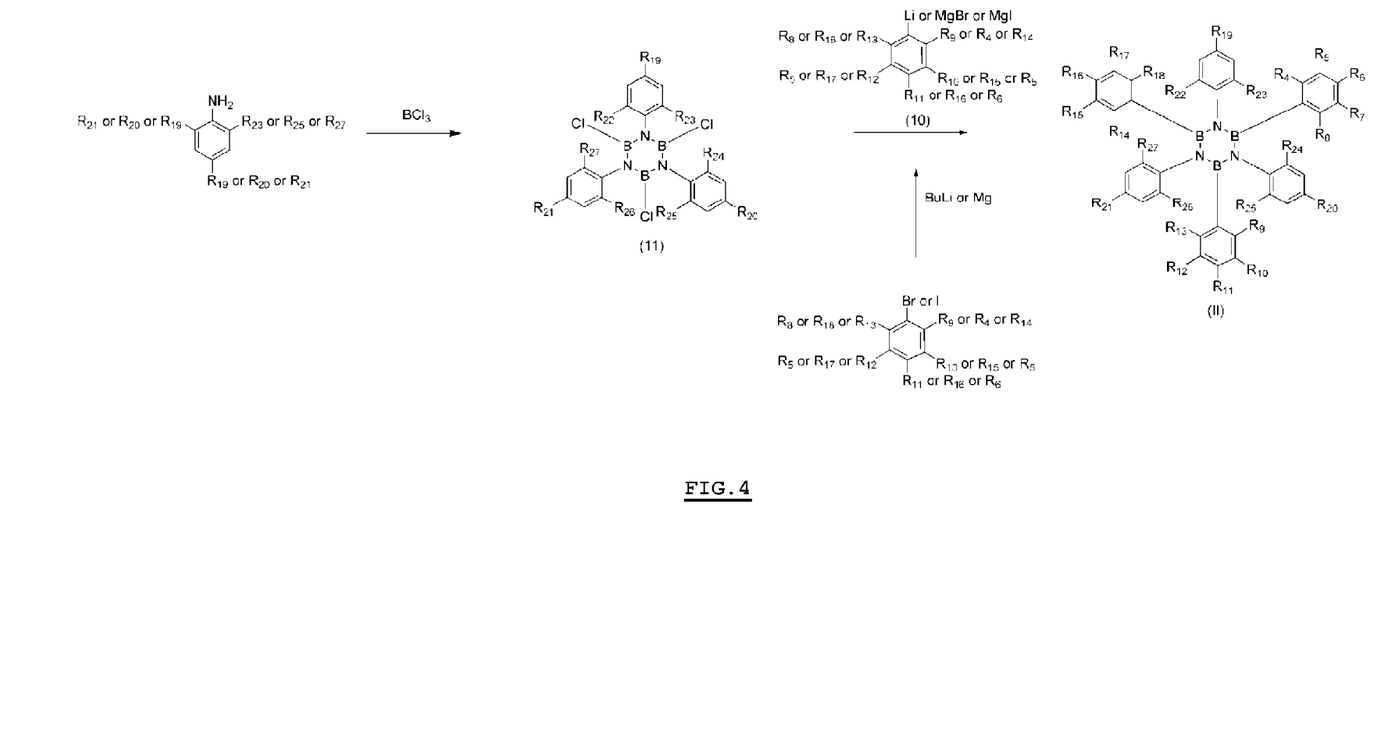
FIG. 4 represents the general synthetic strategy for the formation of borazine derivatives according to formula (II).

Borazine derivatives according to the invention have been surprisingly found to emit in the UV region (typically in a region corresponding to a wavelength comprised between 100 nm and 400 nm) as depicted in FIGS. 2 and 3.

According to a preferred aspect, borazine derivatives according to the invention have the capability to emit (substantially) exclusively in the UV region and are substantially non-emissive in the visible region. This specific property will provide better emission control and color purity when such borazine derivatives are included in e.g. light-emitting devices.

However, some borazine derivatives according to the invention may be capable of additionally emitting (at least partially) in the UV-Visible region.

As previously mentioned, UV light sources may find particular use in various domains, such as optical storage, photocatalysis, sterilization and disinfection of liquids such as water or surgical tools, detection of counterfeiting products, and in various surgical methods or medical treatments such as ophthalmic surgery or epilepsy treatment.

Advantageously, the borazine derivatives according to the invention are capable of emitting (essentially in the UV region) with a surprisingly sharp emission peak. This property allows obtaining UV light sources with very precise emission characteristics, which may be particularly useful in e.g. the field of water treatment/disinfection.

Advantageously, the borazine derivatives according to the invention are capable of emitting in the UV region with surprisingly high quantum yield. Typically, quantum yields of above 0.05, preferably above 0.3, more preferably above 0.4, even more preferably above 0.5, most preferably above 0.6. Quantum yields are typically measured in solution or in solid state.

Advantageously still, the borazine derivatives according to the invention have substituents which allow fine-tuning the electronic properties of the borazine derivatives. In that context, it has been surprisingly found that the borazine derivatives of the invention, by appropriate selection of the substituents linked to the borane and nitrogen atoms of the borazine derivatives, permits fine modulation of the fluorescence/emission properties while preserving emission in the UV region and stability to air, and whilst preserving high quantum yield of the emission.

In the case of borazine derivatives of the invention, this fine-tuning may be performed without detrimentally affecting (interfering or perturbing) the emission properties of the borazine ring per se. As such, the group substituents present in the borazine derivatives of the present invention may be formerly be regarded as "transparent substituents" since they provide minimum contribution to the overall UV emission of the borazine derivative, whereas the main contribution to the overall UV emission of the borazine derivatives may be attributed to the borazine ring. This is important property of the borazine derivatives of the invention which provides better control of the overall UV emission properties, and ultimately improved performance/efficiency of the luminescent devices manufactured with the borazine derivatives.

Advantageously, the borazine derivatives of the invention surprisingly provide excellent processability properties, and allow in particular solution processing and continuous printing (such as e.g. ink jet printing).

Still another surprising advantage of the borazine derivatives of the invention resides in the fact that they possess high charge carrier mobility, including excellent electron and hole mobility properties.

Accordingly, the borazine derivatives according to the invention may advantageously be used in the manufacture of electronic devices, preferably electroluminescent devices and semiconductor devices.

The borazine derivatives of the invention may find particular use in the manufacture of the emissive layer of the electroluminescent device, in particular an organic light-emitting device (OLED). The invention is however not that limited, and the borazine derivatives of the invention may be used/incorporated in other typical layers of electroluminescent layers such as e.g. hole-injection layer, hole-transporting layer, electron-injection layer and electron-transporting layer.

Other applications of the borazine derivatives according to the invention include, but are not limited to, use as flame retardant, use as insulator for capacitors, use as hydrogen material, use for the production of ceramics, use in neutron therapy as neutron capture agent, and use in non-linear optical.

Preferably, in the borazine derivative of the invention as described above, at least one substituent, preferably all the substituents, selected from the group of $R^{22}$, $R^{23}$, $R^{24}$, $R^{25}$, $R^{26}$ and $R^{27}$ are independently selected to be hydrogen.

Preferably, in the borazine derivatives of the invention, at least two substituents, preferably all the substituents, selected from the group of $R^4$, $R^8$, $R^9$, $R^{13}$, $R^{14}$ and $R^{18}$ are independently selected from the group consisting of linear or branched saturated alkyl groups, preferably with 1 to 6 carbon atoms, more preferably with 1 to 4 carbon atoms, even more preferably with 1 to 3 carbon atoms. Exemplary linear or branched saturated alkyl groups for use herein include, but are not limited to, methyl, ethyl, n-propyl, iso-propyl, n-butyl, iso-butyl, tertio-butyl, pentyl and hexyl groups. Still more preferably, in the borazine derivatives of the invention, at least two substituents, preferably all the substituents, selected from the group of $R^4$, $R^8$, $R^9$, $R^{13}$, $R^{14}$ and $R^{18}$ are independently selected from the group consisting of methyl, ethyl, and iso-propyl groups.

Preferably, in the borazine derivatives of the invention, at least one substituent, preferably all the substituents, selected from the group of $R^6$, $R^{11}$ and $R^{16}$ are independently selected from the group consisting of linear or branched saturated alkyl groups and halogens; preferably from the group consisting of linear or branched saturated alkyl groups with 1 to 6 carbon atoms, more preferably with 1 to 4 carbon atoms, even more preferably with 1 to 3 carbon atoms. Exemplary linear or branched saturated alkyl groups for use herein include, but are not limited to, methyl, ethyl, n-propyl, iso-propyl, n-butyl, iso-butyl, tertio-butyl, pentyl and hexyl groups. Still more preferably, in the borazine derivatives of the invention, at least one substituent, preferably all the substituents, selected from the group of $R^6$, $R^{11}$ and $R^{16}$ are independently selected from the group consisting of methyl, ethyl and isopropyl groups.

Preferably, in the borazine derivative of the invention, at least one substituent, preferably all the substituents, selected from the group of $R^{19}$, $R^{20}$ and $R^{21}$ are independently selected from the group consisting of hydrogen, and linear or branched saturated alkyl groups, preferably with 1 to 12 carbon atoms, more preferably with 1 to 6 carbon atoms, even more preferably with 1 to 3 carbon atoms. Exemplary linear or branched saturated alkyl groups for use herein include, but are not limited to, methyl, ethyl, n-propyl, iso-propyl, n-butyl, iso-butyl, tertio-butyl, pentyl, hexyl and dodecyl groups. More preferably, in the borazine derivative of the invention, at least one substituent, preferably all the substituents, selected from the group of $R^{19}$, $R^{20}$ and $R^{21}$ are independently selected from the group consisting of hydrogen and dodecyl groups.

Preferably, in the borazine derivatives of the invention, each of $R^1$ to $R^3$ is independently selected from the group consisting of hydrogen, linear or branched saturated alkyl group, cycloalkyl group, aryl group and aralkyl group. More preferably, in the borazine derivatives of the invention, each of $R^1$ to $R^3$ is independently selected from the group consisting of hydrogen, isopropyl, cyclohexyl and phenyl groups.

According to one preferred aspect, the borazine derivative of the invention is according to formula (II), wherein $R^4$, $R^6$, $R^8$, $R^9$, $R^{11}$, $R^{13}$, $R^{14}$, $R^{16}$ and $R^{18}$ are methyl groups; and wherein $R^5$, $R^7$, $R^{10}$, $R^{12}$, $R^{15}$, $R^{17}$ and $R^{19}$ to $R^{27}$ are selected to be hydrogen. Accordingly, in one preferred aspect, the borazine derivative of the invention is represented by the following formula (1):

(1)

According to another preferred aspect, the borazine derivative of the invention is according to formula (II), wherein $R^4$, $R^6$, $R^8$, $R^9$, $R^{11}$, $R^{13}$, $R^{14}$, $R^{16}$ and $R^{18}$ are methyl groups; wherein $R^5$, $R^7$, $R^{10}$, $R^{12}$, $R^{15}$ and $R^{17}$ and $R^{22}$ to $R^{27}$ are selected to be hydrogen; and wherein $R^{19}$, $R^{20}$, $R^{21}$ are dodecyl groups. Accordingly, in one preferred aspect, the borazine derivative of the invention is represented by the following formula (2):

(2)

According to still another preferred aspect, the borazine derivative of the invention is according to formula (II), wherein $R^4$, $R^5$, $R^7$, $R^8$, $R^9$, $R^{10}$, $R^{12}$, $R^{13}$, $R^{14}$, $R^{15}$, $R^{17}$ and $R^{16}$ and $R^{18}$ are methyl groups; and wherein $R^6$, $R^{11}$, $R^{16}$ and $R^{19}$ to $R^{27}$ are selected to be hydrogen. Accordingly, in one preferred aspect, the borazine derivative of the invention is represented by the following formula (9):

(9)

According to still another preferred aspect, the borazine derivative of the invention is represented by the following formula (10):

(10)

Advantageously, the borazine derivatives according to the present invention may be easily synthesized according to standard and well established synthetic protocols. Suitable synthetic routes will be easily identified by those skilled in the art of synthetic organic chemistry.

One exemplary and suitable synthetic route to the borazine derivatives of the invention is described e.g. by Wakamiya et al. in *J. Am. Chem. Soc.* 2005, 127, 14859.

Figure 5:
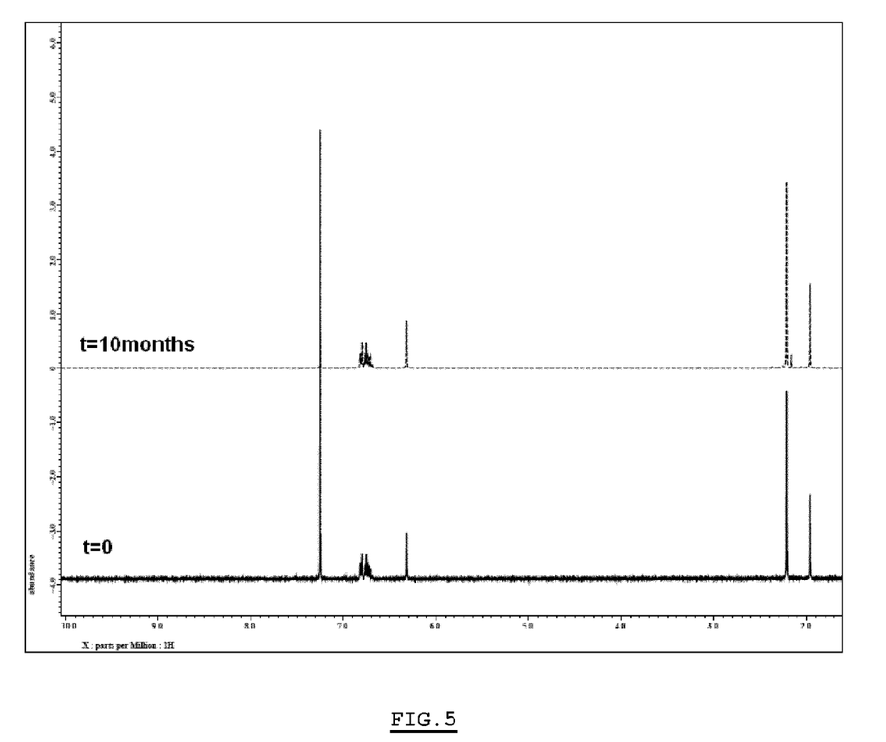
FIG. 5 represents the NMR spectra of borazine derivative (1) at t=0 (top) and at t=10 months (bottom) showing the excellent stability of the compound at air and room temperature.

One general exemplary path for the synthesis of borazine derivatives according to formula (II) involves the condensation reaction of aniline derivative with boron trichloride, forming a borazole intermediate N, N,N"-substituted triphenyl-B,B,B"-trichloro (11) followed by substitution on the boron atoms of the chlorinated borazole by lithiate derivative (10) as described in FIG. 5. FIG. 5 describes the general synthetic strategy for the formation of borazine derivatives according to formula (II), wherein: a) BCl3, anhydrous toluene, reflux, 16 h; b) BuLi, anhydrous THF, −78° C., 1 h 30; c) r.t., 3 h.

According to another aspect, the present invention relates to an electronic device comprising at least one layer comprising a borazine derivative as described above. The electronic device according to the present invention is preferably selected from the group consisting of electroluminescent and semiconductor devices.

In a preferred aspect, the electronic device of the invention is an electroluminescent device, preferably and OLED, wherein the layer is preferably the emissive layer. Alternatively, the layer comprising a borazine derivative of the invention may be any of other typical layers of electroluminescent layers such as e.g. hole-injection layer, hole-transporting layer, electron-injection layer and electron-transporting layer.

According to the preferred aspect wherein the electronic device of the invention is an electroluminescent device, such device comprises preferably at least one layer comprising a borazine derivative as described above.

In another preferred aspect, the electronic device of the invention is a semiconductor device. More preferably, the electronic device of the invention is a transistor.

According to still another aspect of the present invention, it is provided a method for the manufacture of an electronic device which comprises the step of including a borazine derivative as described above, wherein the electronic device is preferably selected from the group consisting of electroluminescent and semiconductor devices.

Preferably, in the method of the present invention, the electronic device is an electroluminescent device, more preferably and OLED. Preferably still, in the method of the present invention the borazine derivative is included in the emissive layer of the OLED. Alternatively, the borazine derivative of the invention may be included in any of other typical layers of electroluminescent layers such as e.g. hole-injection layer, hole-transporting layer, electron-injection layer and electron-transporting layer.

According to the preferred aspect wherein the method of the invention is directed to the manufacture of an electroluminescent device, such method comprises preferably the step of including a borazine derivative as described above.

In another preferred aspect of the method of the present invention, the electronic device is a semiconductor device, more preferably a transistor.

According to still another aspect, the present invention relates to the use of borazine derivatives as described above for the manufacture of an electronic device. Preferably, the borazine derivative of the invention is used for the manufacture of a device selected from the group consisting of electroluminescent and semiconductor devices.

In a preferred aspect, the borazine derivative of the invention is used for the manufacture of an OLED, wherein the borazine derivative is preferably used for the manufacture of the emissive layer of the OLED. Alternatively, borazine derivatives of the invention may be used for the manufacture of other typical layers of electroluminescent layers such as e.g. hole-injection layer, hole-transporting layer, electron-injection layer and electron-transporting layer.

According to the preferred aspect of the invention wherein the manufacture of an electroluminescent device is envisaged, it is preferably made use of borazine derivatives as described above.

In another preferred aspect, the borazine derivatives of the invention are used for the manufacture of a semiconductor device, preferably a transistor.

In still another aspect, the present invention is directed to an organic composition comprising borazine derivatives as above-described. Preferably, the organic composition is an ink composition suitable for use in a continuous printing process, more preferably in an ink jet printing process.

In the context of the present invention, it has been surprisingly found that borazine derivatives according to the invention exhibit excellent solubility in common organic solvents, which makes them suitable for the preparation of e.g. organic inks which can be in turn be used in the manufacture of e.g. OLEDs by e.g. deposition solution. Without being bound by theory, it is believed that the strong (improved) solubility of some of the borazine derivatives according to the invention is due to the presence of substituents, such as e.g. alkyl chains on the corresponding phenyl rings.

EXAMPLES

Example 1

Detailed Synthesis of Borazine Intermediate N,N',N"-triphenyl-B,B,B"-tri(2,4,6-trimethyl)phenyl borazine (1)

Reference: Yamagushi, JACS, 2005, page 14859

In a dry 25 ml Schlenk flask, anhydrous aniline (370 mg, 4 mmoles) is diluted with 8 ml of anhydrous toluene. The solution is allowed to cool down to −5° C. (ice-salt bath). Then boron trichloride (5.2 ml, 5.2 mmoles, 1M solution in toluene) is added dropwise which yields to a white precipitate. The septum is changed for a dry condenser topped by a calcium chloride tube. The reaction mixture is heated up for 16 h. After this period, the flask is cooled down and subject to three freeze-to-thaw cycle to remove the hydrogen chloride.

Preparation of the lithiate: in a dry 50 ml Schlenk flask, bromomesitylene (876 mg, 4.4 mmoles) is diluted with 10 ml of anhydrous THF. The solution is cooled down to −78° C. and freshly titrated buthyl lithium (3.8 ml, 5.2 mmoles) is added dropwise. The flask is allowed to warm up to 0° C. for 1 h. The color changes from transparent to light yellow. The borazine is cannulated dropwise to the lithiate at 0° C. and allowed to react at room temperature. Aliquots are taken after 3 h and 24 h, the NMR analysis shows no changes between the two samples. After 24 h, the reaction is quenched by 20 ml of water. The aqueous layer is extracted three times with 20 ml of ethyl acetate. The organic layer is dried over magnesium sulphate, filtered and the solvents removed with vacuum. The crude is purified by silica gel chromatography, ethyl acetate-cyclohexane (1:5) (Rf=0.5).

The compound crystallizes in:
a) Dichloromethane (r.t., slow evaporation, big needles)
b) Cyclohexane (r.t., slow evaporation, hexagon which brakes when they dry)
c) Pentane, hexane or methyl acetate (5° C., hexagon obtained with cyclohexane slowly convert into this more stable forms, several appearance, pyramid, parallelogram, etc).

$^1$H (400 MHz, CDCl$_3$, 25° C.): δ (ppm) 6.82-6.80 (d of d, 8 Hz, 6H, H$_2$); 6.77-6.71 (m, 9H, H$_3$ and H$_4$); 6.32 (s, 6H, H$_7$); 2.22 (s, 18H, H$_9$) 1.97 (s, 9H, H$_{10}$) $^{13}$C (100 MHz, CDCl$_3$, 25° C.) δ (ppm) 146.4 (C$_1$); 137.3; 136.1; 127.0; 126.7; 126.2; 23.1 (C$_9$); 21.1 (C$_{10}$).

$^{11}$B (100 MHz, CDCl$_3$, 25° C.) δ (ppm) 38-35 (w).

$^1$H (400 MHz, C$_6$D$_6$, 25° C.): δ (ppm) 7.16 (d, 6.8 Hz, 6H, H$_2$); 6.78 (t, 8 Hz, 6H, H$_3$), 6.58 (t, 7.6 Hz, 3H, H$_4$); 6.47 HZ (s, 6H, H$_7$); 2.51 (s, 18H, H$_9$); 1.86 (s, 9H, H$_{10}$).

IR: Solid. KBr. (cm$^{-1}$) 3027 (CH aromatic); 2914; 2854 (CH alkyl); 1611; 1597; 1491; 1359 (B—N) 1308;

Mass spectrometry: C$_{45}$H$_{48}$N$_3$B$_3$, Theory: MM=663.3157; Exact Mass=663.4127.

UV: Solvent: acetonitrile. Absorption maxima: 259 nm (ε=6.4 10$^3$); 265 nm (ε=11 10$^3$); 271 nm (ε=9.7 10$^3$), 217 nm.

Fluorescence: Solvent: acetonitrile. Excitation: 264 nm. Emission: 305 nm.

Solubility:

| Solvent | Milligram/milliliter |
| --- | --- |
| Toluene | 45 |
| Ethyl acetate | 62 |
| Dichloromethane | 102 |
| Chloroform | 54 |

Example 2

Detailed Synthesis of Borazine Intermediate N,N',N"-tri(4-dodecyl)phenyl-B,B,B"-tri(2,4,6-trimethyl)phenyl borazine (2)

Reference: Yamagushi, JACS, 2005, p 14859

In a dry 25 ml Schlenk flask, anhydrous 4-dodecylaniline (261.46 mg, 1 mmoles) is diluted with 8 ml of anhydrous toluene. The solution is allowed to cool down to −5° C. (ice-salt bath). Then boron trichloride (1.3 ml, 1.3 mmoles, 1M solution in toluene) is added dropwise which yields to a white precipitate. The septum is changed for a dry condenser topped by a calcium chloride tube. The reaction mixture is heated up for 18 h. After this period the flask is cooled down and subject to three freeze-to-thaw cycle to remove the hydrogen chloride.

Preparation of the lithiate: in a dry 50 ml Schlenk flask, bromomesitylene (219 mg, 1.1 mmoles) is diluted with 10 ml of anhydrous THF. The solution is cooled down to −78° C. and freshly titrated buthyl lithium (3.8 ml, 5.2 mmoles) is added dropwise. The flask is allowed to warm up to 0° C. for 1 h. The color changes from transparent to light yellow. The borazine is cannulated dropwise to the lithiate at 0° C. and allowed to react at room temperature. After 15 h the reaction was quenched by 20 ml of water. The aqueous layer is extracted three times with 20 ml of ethyl acetate. The organic layer is dried over magnesium sulphate, filtered and the solvents removed with vacuum. The crude is purified by silica gel chromatography, cyclohexane:dichloromethane (1:4) (Rf=0.2).

$^1$H (400 MHz, CDCl$_3$, 25° C.) δ (ppm) 6.66 (d, 8 Hz, 6H, H$_3$); 6.50 (d, 8 Hz, 6H, H$_2$); 6.31 (s, 6H, H$_7$); 2.26 (t, 6.2 Hz, 6H, Ph-CH$_2$—CH$_2$) 2.18 (s, 18H, H$_9$), 1.97 (s 9H, H$_{10}$); 1.32-1.25 (w, 19H, alkyl), 0.88 (t, 6.6 Hz, CH$_2$—CH$_3$).

$^{13}$C (100 MHz, CDCl$_3$, 25° C.) δ (ppm) 143.9 (C$_1$); 138.0; 137.3; 136.9; 135.7; 126.7 (C$_3$); 126.6 (C$_2$), 126.0 (C$_7$); 34.9 (Ph-CH$_2$—CH$_2$); 32.0; 31.0; 29.8; 29.7; 23.1 (C$_9$); 23.0; 21.1 (C$_{10}$); 14.2 (CH$_2$—CH$_3$).

$^{11}$B (100 MHz, CDCl$_3$, 25° C.) δ (ppm) 38-35 (w).

IR: Solid. KBr. (cm$^{-1}$) 2925 (CH aromatic); 2853 (CH alkyl); 1611; 1509; 1438; 1361 (B—N) 1301; 847.

Mass spectrometry: C$_{81}$H$_{120}$N$_3$B$_3$, Theory: MM=1168.2939; Exact Mass=1167.9761

Solubility: The compound is an oil, which is miscible with toluene, ethyl acetate, dichloromethane, benzene and chloroform.

Example 3

Properties of Electroluminescent Devices Comprising a Borazine Derivative According to the Invention Two electroluminescent devices corresponding to a LEC (light-emitting cell—first device) and to a LED (light-emitting diode—second device) were constructed and their emission properties under electrical injection were tested.

The first electroluminescent device corresponding to a LEC (Light-emitting cell) and comprising in its active layer N-triphenyl-B-trimesityl borazine was constructed. More precisely, the device structure was built on an indium-tin oxide (ITO) anode, with an 80 nm hole-injection layer of PEDOT:PSS spin-cast from a 2.8% solution in water (Sigma Aldrich 560596). the active layer consisted of a blend of N-triphenyl-B-trimesityl as the emitter, poly(ethylene oxide) (PEO) as the ion transporter and lithium triflate (LiTr) as the salt providing mobile ions. The solution was spin-cast from a mix of toluene and THF (1:1), with a concentration of 2 wt. % of solids, of which 50 wt. % was N-triphenyl-B-trimesityl, and 50 wt. % PEO:LiTr with a 20:1 molar ratio of the $CH_2CH_2O$ moieties in PEO to LiTr. A low work function anode of LiF (6 nm)/Ca (30 nm)/Al (150 nm) was evaporated on top to facilitate electron injection (for reference see T. M. Brown, R. H. Friend, I. S. Millard, D. J. Lacey, J. H. Burroughes and F. Cacialli. "Efficient electron injection in blue-emitting polymer light-emitting diodes with LiF/Ca/Al cathodes." *Appl. Phys. Lett.* 79, 174-176 (2001); T. M. Brown and F. Cacialli. "Contact Optimisation in Polymer LEDs". *J. Polym. Sci. Pt. B—Polym. Phys.* 41, 2649-2664 (2003)).

The second electroluminescent device corresponding to a LED (light-emitting diode) and comprising also in its active layer N-triphenyl-B-trimesityl borazine (NTPB) was constructed. The device structure was built similarly as for the first electroluminescent device (LEC), but the active layer consisted of N-triphenyl-B-trimesityl borazine and the solution was spin-cast from toluene as a solvent with a 2 wt % concentration of N-triphenyl-B-trimesityl.

Both current-voltage-light characteristics and electroluminescence spectrum were measured for said first and second electroluminescent devices. Results are presented respectively in FIG. 6a and FIG. 6b for the first electroluminescent device (LEC), and in FIGS. 7a and 7b for the second electroluminescent device (LED).

Figure 6:
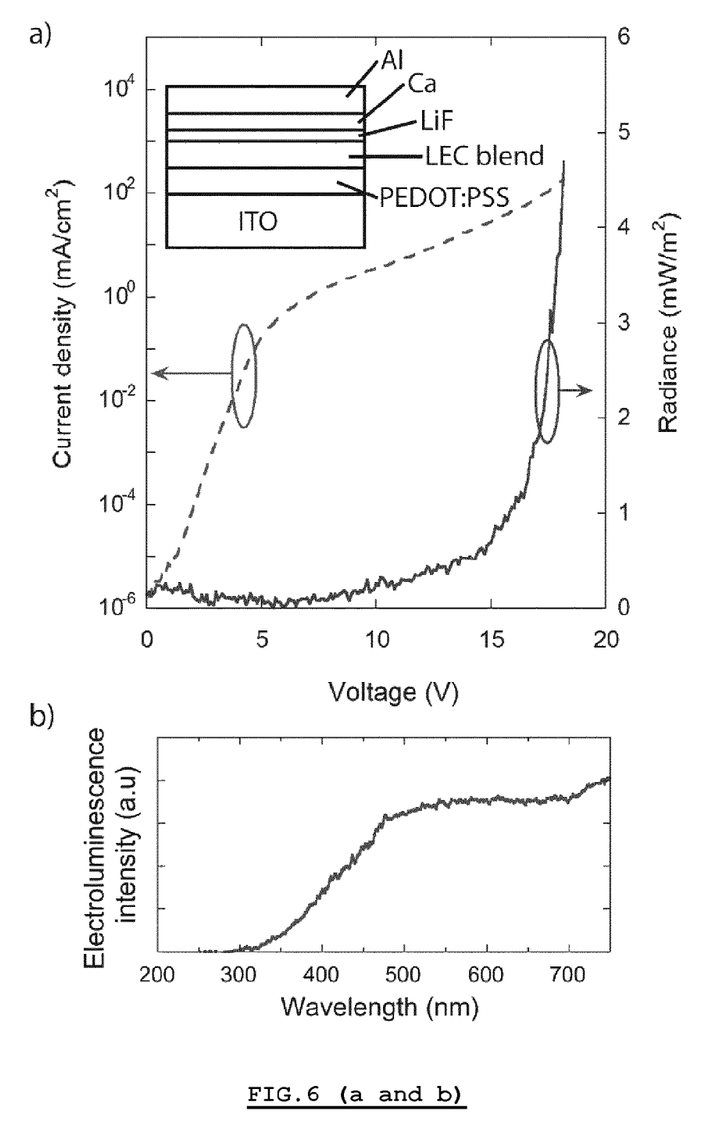

As shown in FIG. 6a, concerning current-voltage-light characteristics, charge injection into the LEC ($1^{st}$ device) was clearly observed, with a strongly non-linear dependence of the current density J on the applied voltage V, as typical for organic and polymeric LEDs. Surprisingly, current densities greater than 100 mA/cm$^2$ were observed at voltages higher than those expected for most molecular diodes and LECs, this probably indicating intrinsic low charge mobility in NTPB and of the existence of further margins for optimization of charge transport and possibly of injection. The current turn-on voltage (arbitrarily defined at $10^{-3}$ mA/cm$^2$) was observed at about 3 V, whereas a clearly observable change of slope in the JV characteristics suggests that bipolar injection was achieved at about 5 V.

Concomitant luminescence was observed with a threshold of ~9.5 V, which is defined as the voltage at which the radiance reaches 0.2 mW/m$^2$.

Figure 7:
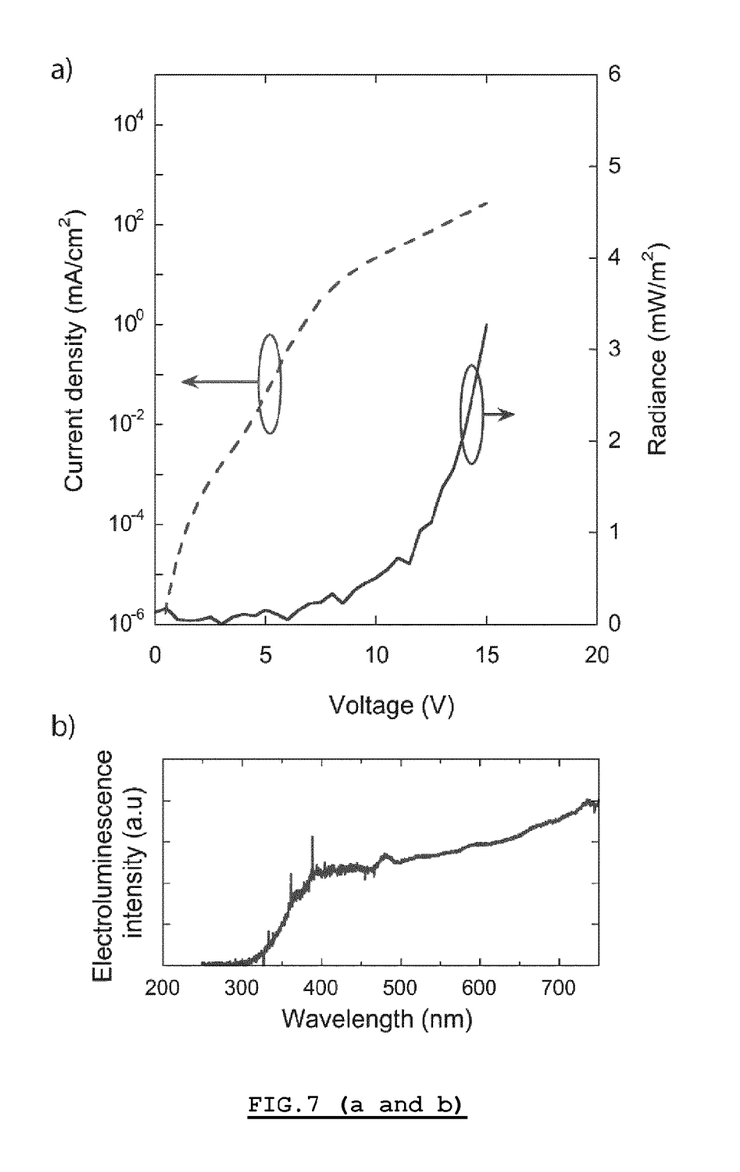
FIG. 7a gives the current-voltage-light characteristics of a light-emitting diode comprising an active layer of N-triphenyl-B-trimesityl as the emitter, blended with poly(ethylene oxide) (PEO) as the ion transporter and lithium triflate (LiTr) as the salt providing mobile ions. The 3.5 mm² device was fabricated with a vertical structure ITO\PEDOT:PSS (80 nm)\active layer\LiF (6 nm)\Ca (30 nm)\Al (150 nm).
FIG. 7b represents the electroluminescence spectrum of the device tested in FIG. 7a obtained at a bias of 13.8 V.

Similar results were found for the LED ($2^{nd}$ electroluminescent device) whose characteristics are reported in FIG. 7a, although the external quantum efficiency was approximately a factor of 10 lower than for the LEC.

Concerning the emission characteristics of the devices, the spectral distribution of the emission of the first device (LEC), as presented in FIG. 14b, clearly demonstrates an emission at wavelengths below 400 nm, albeit with a broad spectrum spanning the whole of the visible range as well. Similar results were found for the second device (LED), the spectrum of which is presented in FIG. 7b. In addition to the potentially interest for white-emitting LEDs and applications in the illumination sector, or for back-lights, it is noted that a very large spectral width is to be expected.

These results show the high promising potential of using borazine derivatives for the manufacture of electroluminescent devices.

The invention claimed is:
1. A borazine derivative represented by the following formula:

wherein the substituents $R^4$ to $R^{18}$ are the same or different from each other;
wherein each of $R^4$ to $R^{18}$ is independently selected from the group consisting of: hydrogen; linear or branched saturated alkyl group; linear or branched unsaturated alkyl group; cycloalkyl group; aryl group; aralkyl group; heteroaryl group; acyl group; hydroxyl; alkoxy group; aryloxy group; acyloxy group; amino group; alkylamino group; arylamino group; acylamino group; cyano group; carboxyl group; thio group; aminocarbonyl group; carbamoyl group, aryloxycarbonyl group, phenoxycarbonyl group, alkoxycarbonyl group and halogen;
wherein $R^4$, $R^8$, $R^9$, $R^{13}$, $R^{14}$ and $R^{18}$ cannot simultaneously be selected to be hydrogen;
wherein $R^4$ to $R^8$ and $R^{14}$ to $R^{18}$ cannot simultaneously be selected to be fluorine;
wherein the substituents $R^{19}$ to $R^{27}$ are the same or different from each other;
wherein each of $R^{19}$ to $R^{27}$ is independently selected from the group consisting of:
hydrogen; linear or branched saturated alkyl group; linear or branched unsaturated alkyl group; cycloalkyl group; aryl group; aralkyl group; heteroaryl group; acyl group; hydroxyl; alkoxy group; aryloxy group; acyloxy group; amino group; alkylamino group; arylamino group; acylamino group; cyano group; carboxyl group; thio group; aminocarbonyl group; carbamoyl group, aryloxycarbonyl group, phenoxycarbonyl group, alkoxycarbonyl group and halogen;
wherein at least one substituent selected from the group of $R^6$, $R^{11}$ and $R^{16}$ is independently selected from the group consisting of linear or branched saturated alkyl groups; and
wherein at least two substituents selected from the group of $R^4$, $R^8$, $R^9$, $R^{13}$, $R^{14}$ and $R^{18}$ are independently selected from the group consisting of linear saturated alkyl groups and branched saturated alkyl groups.

2. A derivative according to claim 1, wherein at least one substituent selected from the group of $R^{22}$, $R^{23}$, $R^{24}$, $R^{25}$, $R^{26}$ and $R^{27}$ is independently selected to be hydrogen.

3. A derivative according to claim 1, wherein at least one substituent selected from the group of $R^{19}$, $R^{20}$ and $R^{21}$ is independently selected from the group consisting of hydrogen, and linear or branched saturated alkyl groups.

4. A derivative according to claim 1, able to emit in the UV region with a quantum yield above 0.05.

5. A derivative according to claim 1, wherein at least one substituent selected from the group of $R^6$, $R^{11}$ and $R^{16}$ is independently selected from the group consisting of linear or branched saturated alkyl groups with 1 to 6 carbon atoms.

6. A derivative according to claim 1, wherein at least one substituent selected from the group of $R^6$, $R^{11}$ and $R^{16}$ is independently selected from the group consisting of linear or branched saturated alkyl groups with 1 to 4 carbon atoms.

7. A derivative according to claim 1, wherein at least one substituent selected from the group of $R^6$, $R^{11}$ and $R^{16}$ is independently selected from the group consisting of linear or branched saturated alkyl groups with 1 to 3 carbon atoms.

8. A derivative according to claim 1, wherein at least two substituents selected from the group of $R^4$, $R^8$, $R^9$, $R^{13}$, $R^{14}$ and $R^{18}$ are independently selected from the group consisting of linear or branched saturated alkyl groups with 1 to 6 carbon atoms.

9. A derivative according to claim 1, wherein at least two substituents selected from the group of $R^4$, $R^8$, $R^9$, $R^{13}$, $R^{14}$ and $R^{18}$ are independently selected from the group consisting of linear or branched saturated alkyl groups with 1 to 4 carbon atoms.

10. A derivative according to claim 1, wherein at least two substituents selected from the group of $R^4$, $R^8$, $R^9$, $R^{13}$, $R^{14}$ and $R^{18}$ are independently selected from the group consisting of linear or branched saturated alkyl groups with 1 to 3 carbon atoms.

11. A derivative according to claim 3, wherein at least one substituent selected from the group of $R^{19}$, $R^{20}$ and $R^{21}$ is independently selected from the group consisting of hydrogen, and linear or branched saturated alkyl groups with 1 to 12 carbon atoms.

12. A derivative according to claim 3, wherein at least one substituent selected from the group of $R^{19}$, $R^{20}$ and $R^{21}$ is independently selected from the group consisting of hydrogen, and linear or branched saturated alkyl groups with 1 to 6 carbon atoms.

13. A derivative according to claim 3, wherein at least one substituent selected from the group of $R^{19}$, $R^{20}$ and $R^{21}$ is independently selected from the group consisting of hydrogen, and linear or branched saturated alkyl groups with 1 to 3 carbon atoms.

* * * * *